United States Patent
Hagiwara

(10) Patent No.: US 6,873,679 B2
(45) Date of Patent: Mar. 29, 2005

(54) MULTI-ROW DETECTOR X-RAY CT APPARATUS

(75) Inventor: Akira Hagiwara, Tokyo (JP)

(73) Assignee: GE Medical Systems Global Technology, LLC, Waukesha, WI (US)

( * ) Notice: Subject to any disclaimer, the term of this patent is extended or adjusted under 35 U.S.C. 154(b) by 57 days.

(21) Appl. No.: 10/639,717

(22) Filed: Aug. 12, 2003

(65) Prior Publication Data
US 2004/0047449 A1 Mar. 11, 2004

(30) Foreign Application Priority Data
Aug. 13, 2002 (JP) ........................................ 2002-235561

(51) Int. Cl.$^7$ ................................................. A61B 6/03
(52) U.S. Cl. ............................ 378/19; 378/15; 378/901
(58) Field of Search ........................... 378/4, 8, 15, 19, 378/901

(56) References Cited

U.S. PATENT DOCUMENTS

| | | |
|---|---|---|
| 5,708,691 A | 1/1998 | Zmora |
| 5,825,842 A | 10/1998 | Taguchi |
| 6,324,246 B1 * | 11/2001 | Ruimi ........................ 378/15 |
| 6,343,108 B1 | 1/2002 | Heuscher |
| 6,445,764 B2 | 9/2002 | Gohno et al. |
| 6,459,754 B1 | 10/2002 | Besson et al. |
| 6,522,714 B1 * | 2/2003 | Wang et al. .................. 378/15 |
| 6,542,570 B1 | 4/2003 | Silver |
| 6,574,298 B2 | 6/2003 | Heuscher |
| 2003/0097063 A1 * | 5/2003 | Wang et al. ................ 600/425 |

* cited by examiner

*Primary Examiner*—David V Bruce
(74) *Attorney, Agent, or Firm*—Carl B. Horton, Esq.; Armstrong Teasdale, LLP

(57) ABSTRACT

For the purpose of obtaining an image having a large slice thickness, such as a thickness twice or three times the size of a multi-row detector as measured in the Z'-axis direction, based on raw data collected by an axial scan or helical scan using the detector, raw data (d1–d6) of three or more adjacent detector rows collected using a multi-row detector (24) having three or more detector rows are multiplied by cone-beam reconstruction weights (Wi) and Z-filter weights (wi), and are added to obtain one projection datum (Dg). Backprojection processing is applied to the projection datum (Dg) to obtain a pixel datum.

4 Claims, 13 Drawing Sheets

Channel Direction

Detector row direction $Dg = wa \cdot Wa \cdot d1 + wb \cdot Wb \cdot d2$ $wa = \dfrac{b}{a+b} \quad wb = \dfrac{a}{a+b}$

MULTI-ROW DETECTOR X-RAY CT APPARATUS

CROSS REFERENCE TO RELATED APPLICATIONS

This application claims the benefit of Japanese Application No. 2002-235561 filed Aug. 13, 2002.

BACKGROUND OF THE INVENTION

The present invention relates to a projection data generating method, a pixel data generating method, and a multi-row detector X-ray CT (computed tomography) apparatus, and more particularly to a method of generating projection data for use in producing an image having a large slice thickness, based on raw data collected by an axial scan or helical scan using a multi-row detector, a method of generating pixel data for the image having a large slice thickness, and a multi-row detector X-ray CT apparatus.

FIG. 14 is a flow chart showing pixel data generating processing in a conventional multi-row detector X-ray CT apparatus.

At Step J1, raw data is collected while rotating an X-ray tube and a multi-row detector around a subject to be imaged.

At Step J2, raw data d1 and d2 corresponding to a pixel g in a reconstruction field P are obtained as shown in FIG. 15. Specifically, the raw data d1 and d2 are obtained from two detector rows that lie closest to a point at which a straight line Lg passing through a focal spot of an X-ray tube 21 and the pixel g in the reconstruction field P intersects a multi-row detector 24. The raw data d1 and d2 are then multiplied by cone-beam reconstruction weights Wa and Wb and Z-filter weights wa and wb and are added to calculate a projection datum Dg corresponding to the pixel g in the reconstruction field P.

The cone-beam reconstruction weight Wa is defined as $(r1/r0)^2$, where the distance from the focal spot of the X-ray tube 21 to a detector row j, channel i of the multi-row detector 24 that corresponds to the raw data d1 is represented as r0, and the distance from the focal spot of the X-ray tube 21 to the pixel g in the reconstruction field corresponding to the raw data d1 is represented as r1.

The cone-beam reconstruction weight Wb is similarly defined.

The Z-filter weights wa and wb are defined as $wa=b/(a+b)$ and $wb=a/(a+b)$, where the distance between the point at which the straight line Lg intersects the multi-row detector 24 and a point corresponding to the raw data d1 as measured in the Z-direction of the detector is represented as a, and the distance between the point at which the straight line Lg intersects the multi-row detector 24 and a point corresponding to the raw data d2 as measured in the Z-direction of the detector is represented as b. These are weights as delineated by a Z-filter Fz shown in FIG. 16.

Referring again to FIG. 14, at Step J3, backprojection processing is applied to the projection datum Dg to calculate a pixel datum Gg.

An image obtained by the conventional multi-row detector X-ray CT apparatus has a slice thickness approximately equal to the size of the detector as measured in the Z-axis direction.

There has been a problem that an image cannot be obtained with a large slice thickness, such as a thickness twice or three times the size of the detector as measured in the Z-axis direction.

SUMMARY OF THE INVENTION

It is therefore an object of the present invention to provide a method of generating projection data for use in producing an image having a large slice thickness, based on raw data collected using a multi-row detector, a method of generating pixel data for the image having a large slice thickness, and a multi-row detector X-ray CT apparatus.

In accordance with its first aspect, the present invention provides a projection data generating method characterized in comprising: multiplying raw data of three or more adjacent detector rows collected using a multi-row detector having three or more detector rows, by cone-beam reconstruction weights and Z-filter weights, and adding the multiplied raw data to obtain one projection datum.

In the projection data generating method of the first aspect, raw data of three or more adjacent detector rows are multiplied by Z-filter weights and added to generate one projection datum. By then applying backprojection processing to such projection data, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained.

The Z-filter weights are defined by a Z-filter for multi-point interpolation for three or more points known in the art (e.g., Hanning interpolation or cubic interpolation).

In accordance with its second aspect, the present invention provides a pixel data generating method characterized in comprising: applying backprojection processing to the projection data generated by the projection data generating method having the aforementioned configuration to obtain pixel data.

In the pixel data generating method of the second aspect, raw data of three or more adjacent detector rows are multiplied by Z-filter weights and added to generate one projection datum, and backprojection processing is applied to such projection data to obtain pixel data; therefore, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained.

In accordance with its third aspect, the present invention provides a projection data generating method characterized in comprising: generating an i-th projection datum corresponding to a pixel in a reconstruction field from raw data of k adjacent detector rows for an i-th rotation among raw data collected by a helical scan in which a multi-row detector having two or more detector rows is employed and $k (\geq 2)$ or more rows go forward per rotation; repeating the generation of the i-th projection datum for $i=1–n, n \geq 2$; and multiplying first—n-th projection data by Z-filter weights and adding the multiplied projection data to obtain one projection datum.

In the projection data generating method of the third aspect, raw data of k adjacent detector rows are multiplied by Z-filter weights and are added to generate one projection datum for each rotation of a helical scan, and the projection data for the rotations are multiplied by Z-filter weights and added to obtain one projection datum. By then applying backprojection processing to such projection data, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained.

The Z-filter weights are defined by a Z-filter for two-point interpolation or for multi-point interpolation for three or more points known in the art.

In accordance with its fourth aspect, the present invention provides the projection data generating method having the aforementioned configuration, characterized in that: k=2, and the i-th projection datum is generated by multiplying raw data of two adjacent detector rows by cone-beam reconstruction weights and Z-filter weights, and adding the multiplied raw data.

In the projection data generating method of the fourth aspect, a Z-filter for two-point interpolation known in the art can be employed to generate a projection datum for each rotation.

In accordance with its fifth aspect, the present invention provides the projection data generating method having the aforementioned configuration, characterized in that: k=3, and the i-th projection datum is generated by multiplying raw data of k adjacent detector rows by cone-beam reconstruction weights and Z-filter weights, and adding the multiplied raw data.

In the projection data generating method of the fifth aspect, a Z-filter for multi-point interpolation for three or more points known in the art can be employed to generate a projection datum for each rotation.

In accordance with its sixth aspect, the present invention provides a pixel data generating method characterized in comprising: applying backprojection processing to the projection data generated by the projection data generating method having the aforementioned configuration to obtain pixel data.

In the pixel data generating method of the sixth aspect, raw data of k adjacent detector rows are multiplied by Z-filter weights and are added to generate one projection datum for each rotation of a helical scan, the projection data for the rotations are multiplied by Z-filter weights and added to obtain one projection datum, and backprojection processing is applied to such projection data to obtain pixel data; therefore, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained.

In accordance with its seventh aspect, the present invention provides a pixel data generating method characterized in comprising: generating an i-th pixel datum corresponding to a pixel in an i-th reconstruction field from raw data of k adjacent detector rows among raw data collected using a multi-row detector having two or more detector rows; repeating the generation of the i-th pixel datum for i=1–n, n≧2; and multiplying first—n-th pixel data by Z-filter weights and adding the multiplied pixel data to obtain one pixel datum.

In the pixel data generating method of the seventh aspect, a pixel datum is generated from raw data of k adjacent detector rows for each of first—n-th reconstruction fields, and the pixel data for the reconstruction fields are multiplied by Z-filter weights and added to obtain one pixel datum; therefore, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained. In addition, an image for each reconstruction field can be obtained.

In accordance with its eighth aspect, the present invention provides the pixel data generating method having the aforementioned configuration, characterized in that: k=2, and the i-th pixel datum is generated by multiplying raw data of two adjacent detector rows by cone-beam reconstruction weights and Z-filter weights, adding the multiplied raw data to obtain an i-th projection datum, and applying backprojection processing to the i-th projection datum.

In the pixel data generating method of the eighth aspect, pixel data for each reconstruction field can be obtained using processing quite the same as the conventional technique.

In accordance with its ninth aspect, the present invention provides a projection data generating method characterized in comprising: generating an i-th projection datum corresponding to a pixel in an i-th reconstruction field from raw data of k (k≧2) adjacent detector rows among raw data collected using a multi-row detector having two or more detector rows; repeating the generation of the i-th projection datum for i=1–n, n≧2; and multiplying first—n-th projection data by Z-filter weights and adding the multiplied projection data to obtain one projection datum.

In the projection data generating method of the ninth aspect, a projection datum is generated from raw data of k adjacent detector rows for each of first—n-th reconstruction fields, and the projection data for the reconstruction fields are multiplied by Z-filter weights and added to obtain one projection datum. By then applying backprojection processing to such projection data, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained.

In accordance with its tenth aspect, the present invention provides the projection data generating method having the aforementioned configuration, characterized in that: k=2, and the i-th projection datum is generated by multiplying raw data of two adjacent detector rows by cone-beam reconstruction weights and Z-filter weights, and adding the multiplied raw data.

In the projection data generating method of the tenth aspect, projection data for each reconstruction field can be obtained using processing quite the same as the conventional technique.

In accordance with its eleventh aspect, the present invention provides a pixel data generating method characterized in comprising: applying backprojection processing to the projection data generated by the projection data generating method having the aforementioned configuration to obtain pixel data.

In the pixel data generating method of the eleventh aspect, a projection datum is generated from raw data of k adjacent detector rows for each of first—n-th reconstruction fields, the projection data for the reconstruction fields are multiplied by Z-filter weights and added to obtain one projection datum, and backprojection processing is applied to such projection data to obtain pixel data; therefore, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained.

In accordance with its twelfth aspect, the present invention provides a multi-row detector X-ray CT apparatus characterized in comprising: an X-ray tube; a multi-row detector having three or more detector rows; scanning means for collecting raw data while rotating at least one of said X-ray tube and said multi-row detector around a subject to be imaged or while rotating at least one of them and at the same time linearly moving both of them relative to the subject to be imaged; projection data generating means for multiplying raw data of three or more adjacent detector rows by cone-beam reconstruction weights and Z-filter weights, and adding the multiplied raw data to obtain one projection datum; and backprojection processing means for applying backprojection processing to the projection data to obtain pixel data.

In the multi-row detector X-ray CT apparatus of the twelfth aspect, the projection data generating method of the first aspect and the pixel data generating method of the second aspect can be suitably implemented.

In accordance with its thirteenth aspect, the present invention provides a multi-row detector X-ray CT apparatus characterized in comprising: an X-ray tube; a multi-row detector having two or more detector rows; scanning means for collecting raw data while rotating at least one of said X-ray tube and said multi-row detector around a subject to be imaged or while rotating at least one of them and at the same time linearly moving both of them relative to the subject to be imaged; projection data generating means for generating an i-th projection datum corresponding to a pixel in a reconstruction field from raw data of k adjacent detector rows for an i-th rotation among raw data collected by a helical scan in which k ($\geq 2$) or more rows go forward per rotation, repeating the generation of the i-th projection datum for i=1–n, n$\geq$2, and next multiplying first—n-th projection data by Z-filter weights and adding the multiplied projection data to obtain one projection datum; and backprojection processing means for applying backprojection processing to the projection data to obtain pixel data.

In the multi-row detector X-ray CT apparatus of the thirteenth aspect, the projection data generating method of the third—fifth aspects and the pixel data generating method of the sixth aspect can be suitably implemented.

In accordance with its fourteenth aspect, the present invention provides the multi-row detector X-ray CT apparatus having the aforementioned configuration, characterized in that: k=2, and said projection data generating means generates the i-th projection datum by multiplying raw data of two adjacent detector rows by cone-beam reconstruction weights and Z-filter weights, and adding the multiplied raw data.

In the multi-row detector X-ray CT apparatus of the fourteenth aspect, the projection data generating method of the fourth aspect can be suitably implemented.

In accordance with its fifteenth aspect, the present invention provides a multi-row detector X-ray CT apparatus characterized in comprising: an X-ray tube; a multi-row detector having two or more detector rows; scanning means for collecting raw data while rotating at least one of said X-ray tube and said multi-row detector around a subject to be imaged or while rotating at least one of them and at the same time linearly moving both of them relative to the subject to be imaged; pixel data generating means for generating an i-th pixel datum corresponding to a pixel in an i-th reconstruction field from raw data of k (k$\geq$2) adjacent detector rows among the raw data, repeating the generation of the i-th pixel datum for i=1–n, n$\geq$2, and next multiplying first—n-th pixel data by Z-filter weights and adding the multiplied pixel data to obtain one pixel datum.

In the multi-row detector X-ray CT apparatus of the fifteenth aspect, the pixel data generating method of the seventh and eighth aspects can be suitably implemented.

In accordance with its sixteenth aspect, the present invention provides a multi-row detector X-ray CT apparatus characterized in comprising: an X-ray tube; a multi-row detector having two or more detector rows; scanning means for collecting raw data while rotating at least one of said X-ray tube and said multi-row detector around a subject to be imaged or while rotating at least one of them and at the same time linearly moving both of them relative to the subject to be imaged; projection data generating means for generating an i-th projection datum corresponding to a pixel in an i-th reconstruction field from raw data of k (k$\geq$2) adjacent detector rows among the raw data, repeating the generation of the i-th projection datum for i=1–n, n$\geq$2, and then multiplying first—n-th projection data by Z-filter weights and adding the multiplied projection data to obtain one projection datum; and backprojection processing means for applying backprojection processing to the projection data to obtain pixel data.

In the multi-row detector X-ray CT apparatus of the sixteenth aspect, the projection data generating method of the ninth and tenth aspects and the pixel data generating method of the eleventh aspect can be suitably implemented.

According to the projection data generating method, pixel data generating method, and multi-row detector X-ray CT apparatus of the present invention, an image having a large slice thickness, such as a thickness twice or three times the size of the detector as measured in the Z-axis direction, can be obtained based on raw data collected by an axial scan or helical scan using a multi-row detector. Moreover, an image having an arbitrary slice thickness, such as a thickness 1.2 or 2.5 times the size of the detector as measured in the Z-axis direction, can be obtained.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to embodiments shown in the accompanying drawings.

First Embodiment

Figure 1:
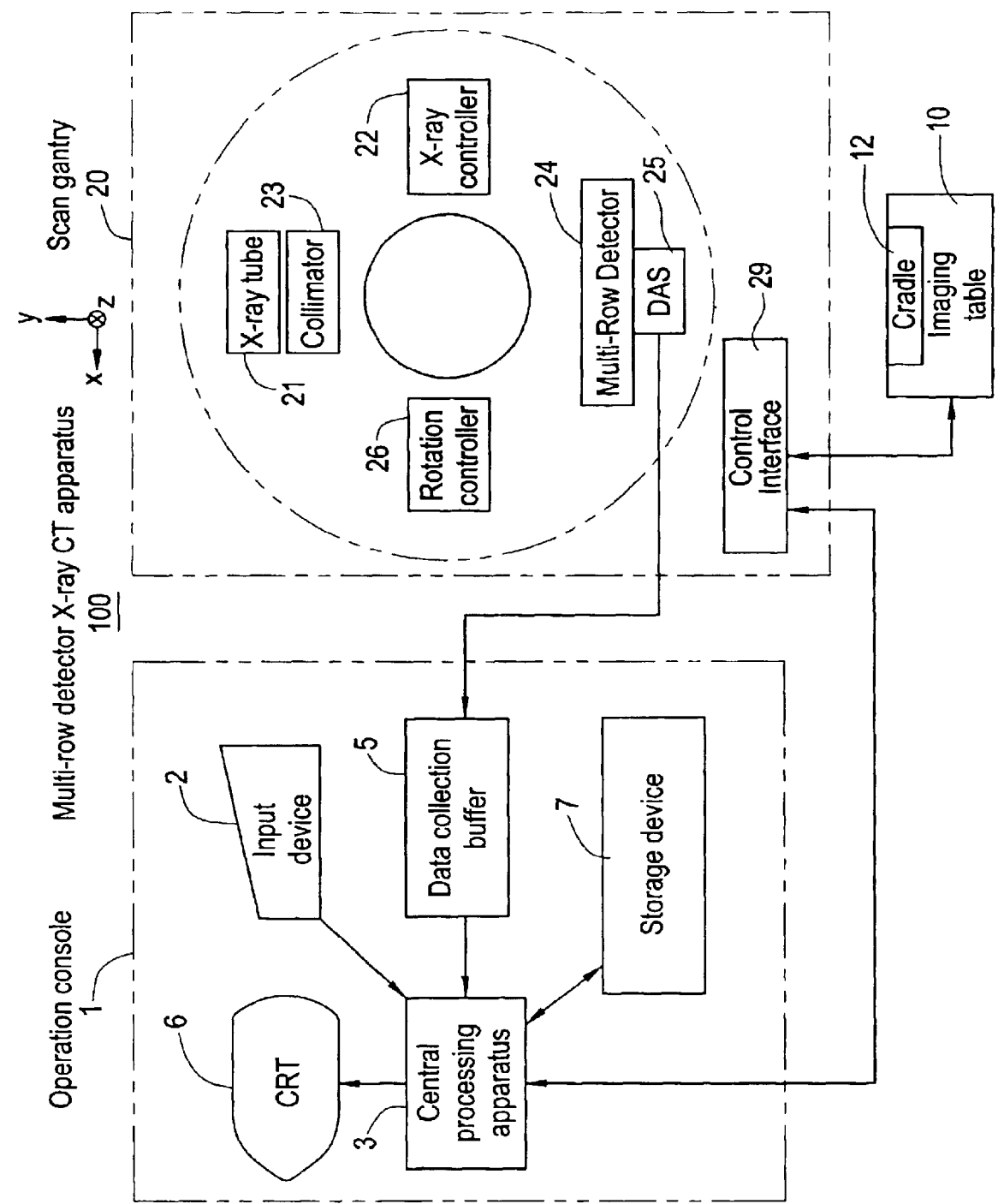
FIG. 1 is a block diagram showing a multi-row detector X-ray CT apparatus in accordance with the present invention.

FIG. 1 is a block diagram of the configuration of a multi-row detector X-ray CT apparatus in accordance with a first embodiment of the present invention.

The multi-row detector X-ray CT apparatus 100 comprises an operation console 1, an imaging table 10, and a scan gantry 20.

The operation console 1 comprises an input device 2 for accepting inputs by a human operator, a central processing apparatus 3 for executing projection data generating processing and pixel data generating processing in accordance with the present invention, a data collection buffer 5 for collecting projection data acquired at the scan gantry 20, a CRT 6 for displaying a CT image reconstructed from the projection data, and a storage device 7 for storing programs, data, and X-ray CT images.

The table apparatus 10 comprises a cradle 12 for laying thereon a subject and transporting the subject into/out of a bore (cavity portion) of the scan gantry 20. The cradle 12 is driven by a motor incorporated in the table apparatus 10.

The scan gantry 20 comprises an X-ray tube 21, an X-ray controller 22, a collimator 23, a multi-row detector 24, a DAS (data acquisition system) 25, a rotation controller 26 for rotating the X-ray tube 21 etc. around the body axis of the subject, and a control interface 29 for communicating control signals etc. with the operation console 1 and imaging table 10.

Figure 2:
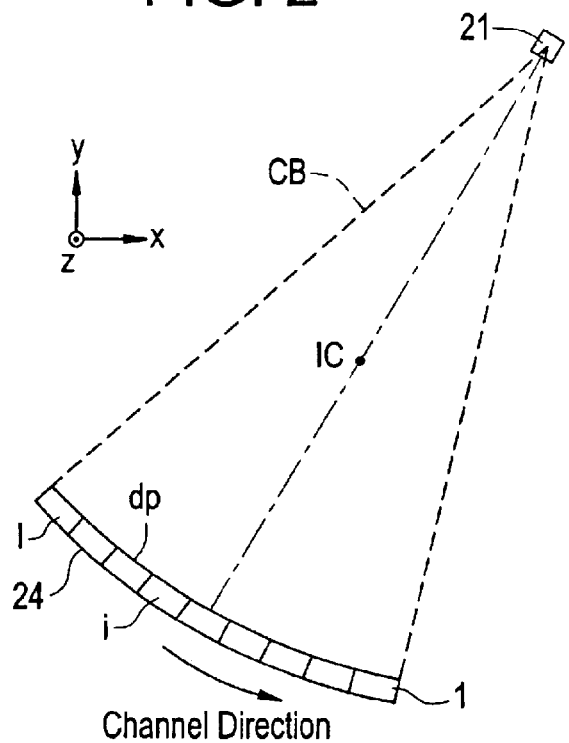
FIG. 2 is an explanatory diagram showing a rotation of an X-ray tube and a multi-row detector.
Figure 3:
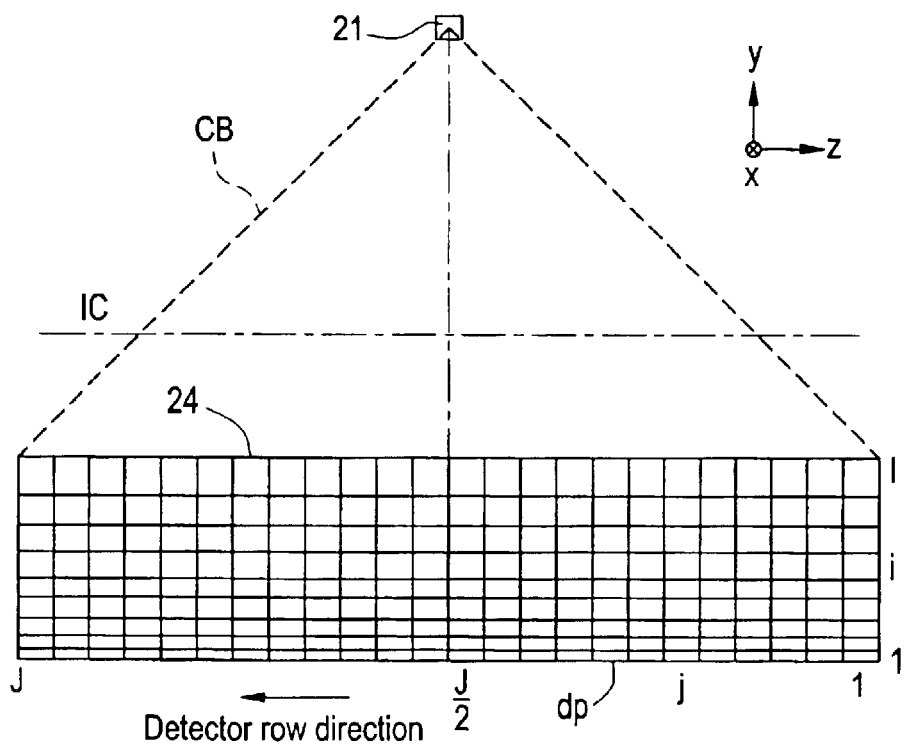
FIG. 3 is an explanatory diagram showing a cone beam.

FIGS. 2 and 3 are explanatory diagrams of the X-ray tube 21 and the multi-row detector 24.

The X-ray tube 21 and multi-row detector 24 rotate around a center of rotation IC. When a vertical direction is represented as a y-direction, a horizontal direction is represented as an x-direction, and a direction perpendicular to both is represented as a z-direction, a plane of rotation of the X-ray tube 21 and multi-row detector 24 is an x-y plane. The direction of movement of the cradle 12 is the z-direction.

The X-ray tube 21 generates an X-ray beam generally referred to as a cone beam CB.

The multi-row detector 24 has, for example, 256 detector rows (J=256). Each detector row has, for example, 1,024 channels (I=1,024).

Figure 4:
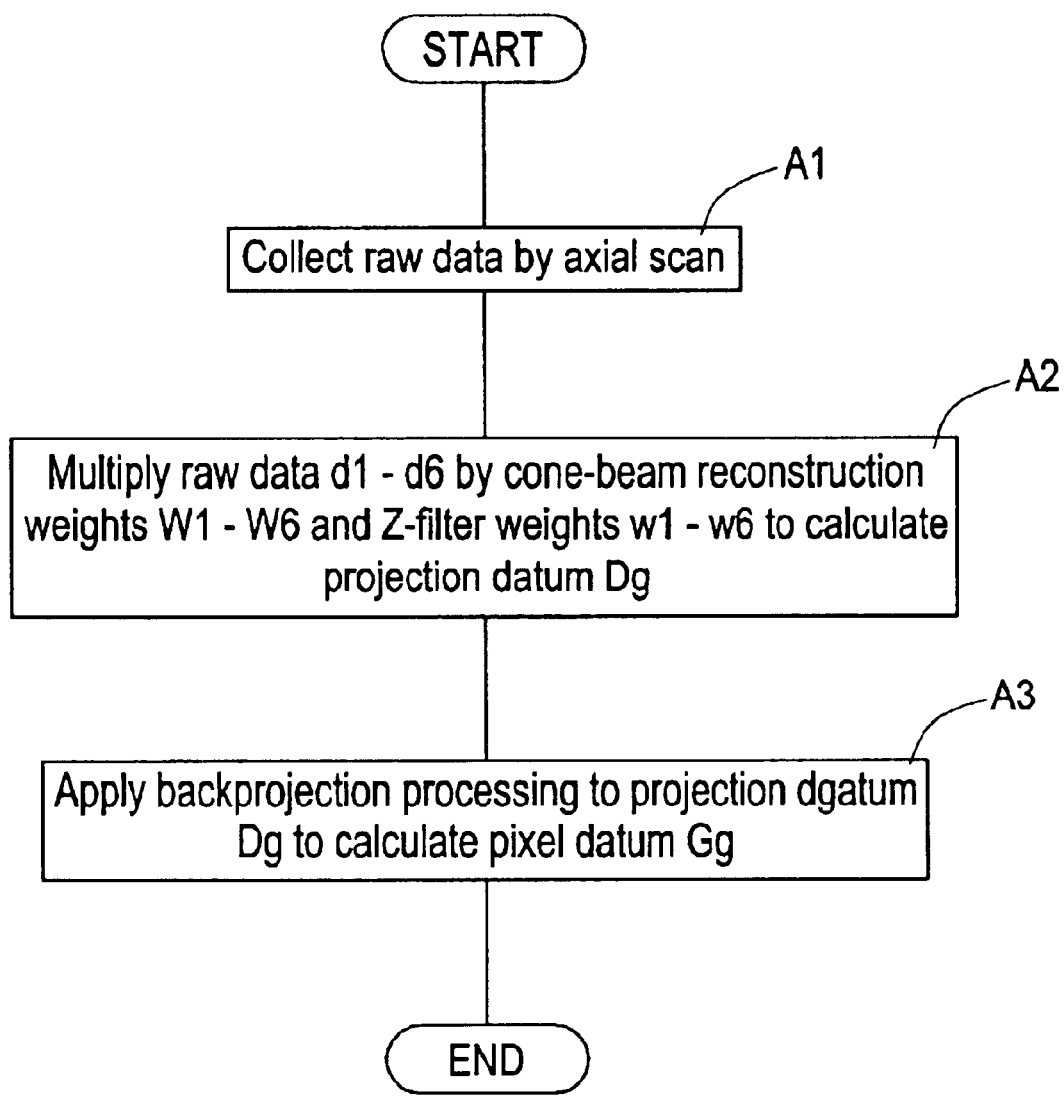
FIG. 4 is a flow chart showing pixel data generating processing in accordance with a first embodiment.

FIG. 4 is a flow chart showing image data generating processing in accordance with the first embodiment.

At Step A1, raw data dj(view, i) represented by a view angle view, detector row index j, and channel index i are collected while rotating the X-ray tube 21 and multi-row detector 24 around the subject to be imaged.

Figure 5:
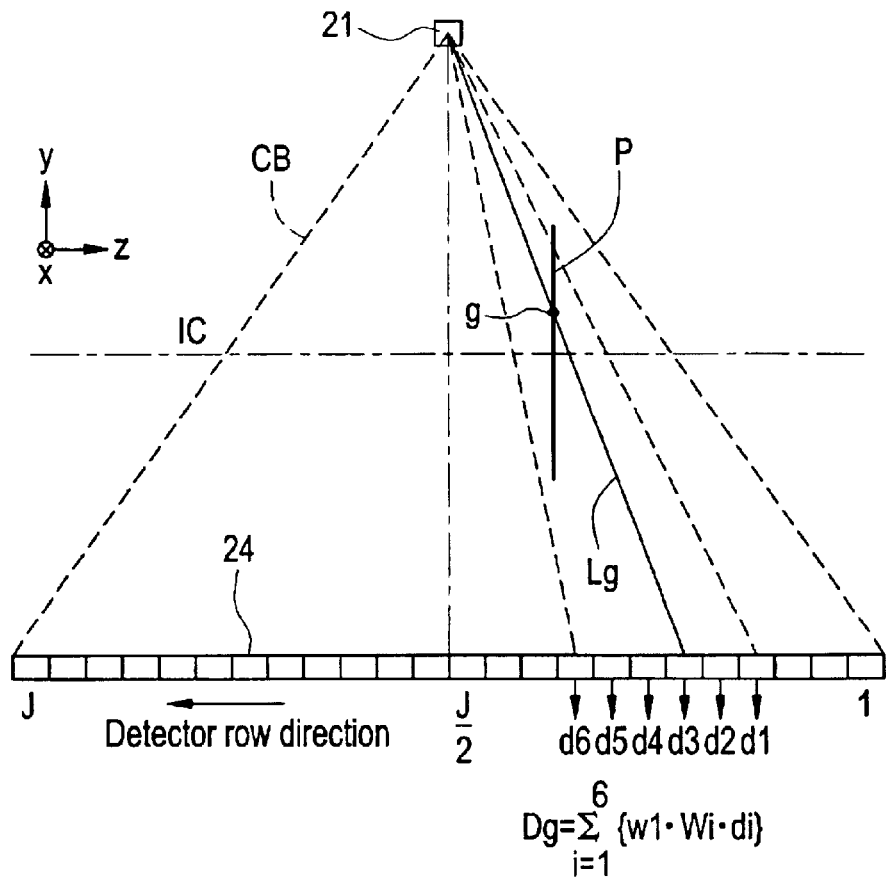
FIG. 5 is a conceptual diagram showing raw data corresponding to a reconstruction field in the first embodiment.

At Step A2, raw data d1–d6 corresponding to a pixel g in a reconstruction field P are obtained as shown in FIG. 5. Specifically, the raw data d1–d6 are obtained from six detector rows that lie closest to a point at which a straight line Lg passing through a focal spot of the X-ray tube 21 and the pixel g in the reconstruction field P intersects the multi-row detector 24. The raw data d1–d6 are then multiplied by cone-beam reconstruction weights W1–W6 and Z-filter weights w1–w6 and are added to calculate a projection datum Dg corresponding to the pixel g in the reconstruction field P.

The cone-beam reconstruction weight W1 is defined as $(r1/r0)^2$, where the distance from the focal spot of the X-ray tube 21 to a detector row j, channel i of the multi-row detector 24 that corresponds to the raw data d1 is represented as r0, and the distance from the focal spot of the X-ray tube 21 to the pixel g in the reconstruction field corresponding to the raw data d1 is represented as r1.

The cone-beam reconstruction weights W2–W6 are similarly defined.

Figure 6:
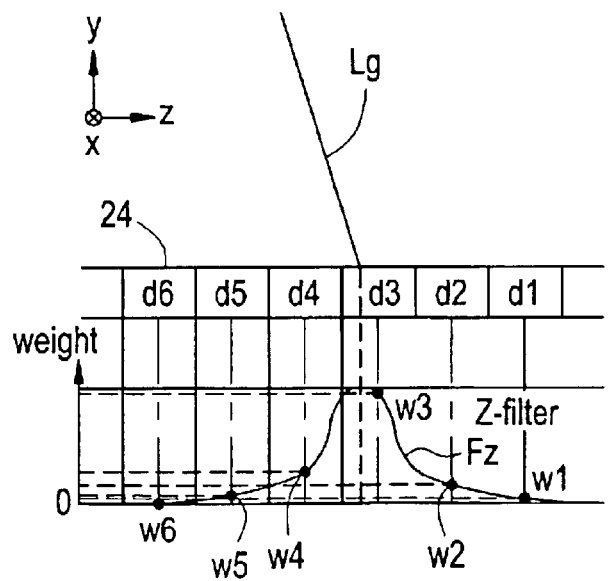
FIG. 6 is a conceptual diagram showing a Z-filter in the first embodiment.

The Z-filter weights w1–w6 are defined by a Z-filter for six-point interpolation known in the art, and are defined by a Z-filter Fz as exemplary shown in FIG. 6.

Referring again to FIG. 4, at Step A3, backprojection processing is applied to the projection datum Dg to calculate a pixel datum Gg.

According to the multi-row detector X-ray CF apparatus 100 of the first embodiment, the raw data d1–d6 of six adjacent detector rows are multiplied by the Z-filter weights w1–w6 and are added to calculate one projection datum Dg, and backprojection processing is applied to such projection data Dg to calculate pixel data Gg; therefore, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained.

Although the raw data d1–d6 of six adjacent detector rows are employed in this embodiment, the process can be similarly applied to a case in which raw data of three or more adjacent detector rows are employed.

Second Embodiment

Figure 7:
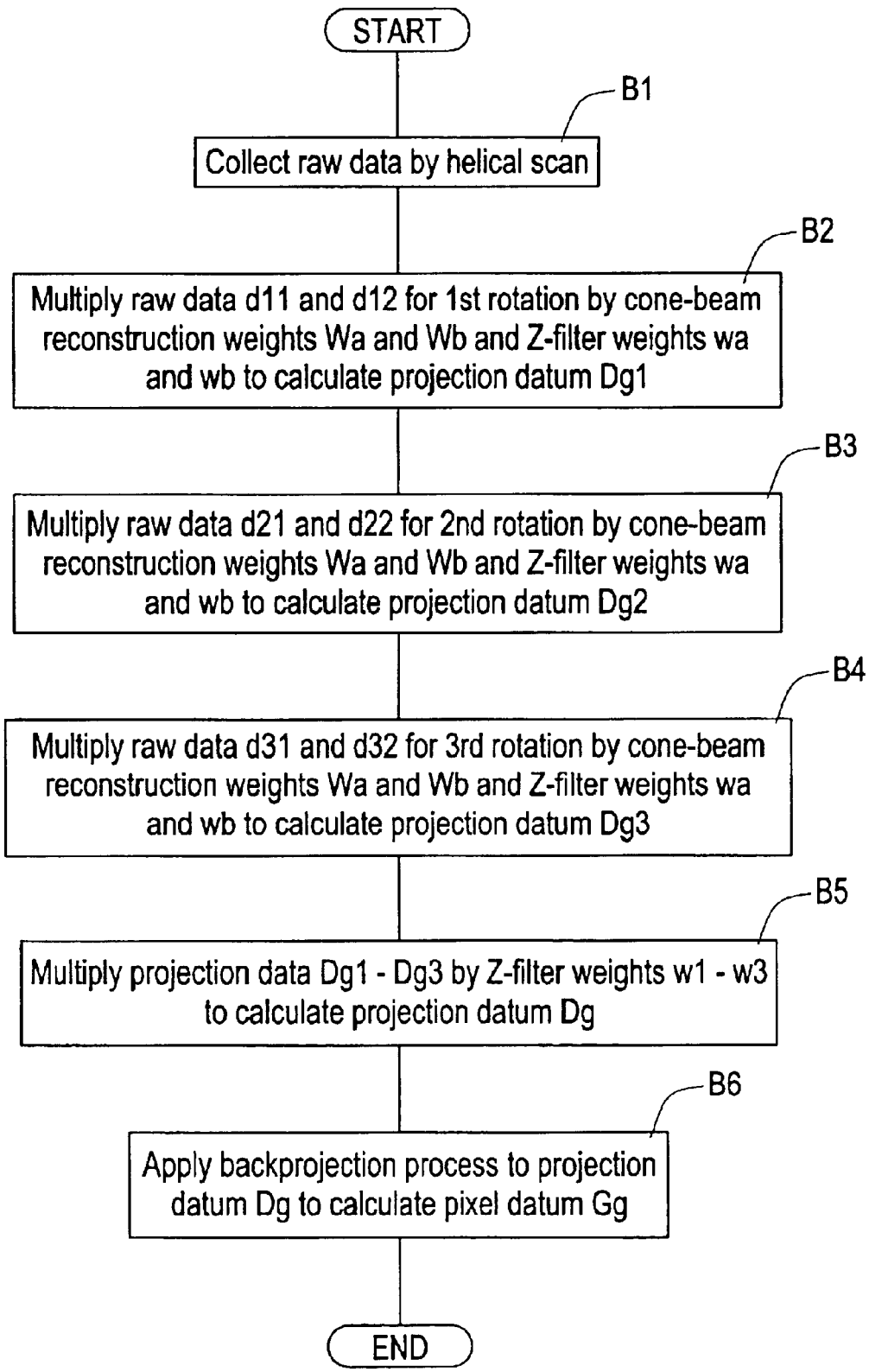
FIG. 7 is a flow chart showing pixel data generating processing in accordance with a second embodiment.

FIG. 7 is a flow chart showing image data generating processing in accordance with a second embodiment.

At Step B1, raw data dj(view, δ, i) represented by a view angle view, relative angular difference δ, detector row index j, and channel index i are collected while rotating the X-ray tube 21 and multi-row detector 24 around the subject to be imaged and linearly moving the cradle 12.

The relative angular difference δ is a parameter indicating the number of rotations at the same view angle, and for example, is represented as δ=0° for a first rotation, δ=360° for a second rotation, δ=720° for a third rotation, and so forth.

The cradle 12 is configured to linearly move by an amount corresponding to two detector rows per rotation.

Figure 8:
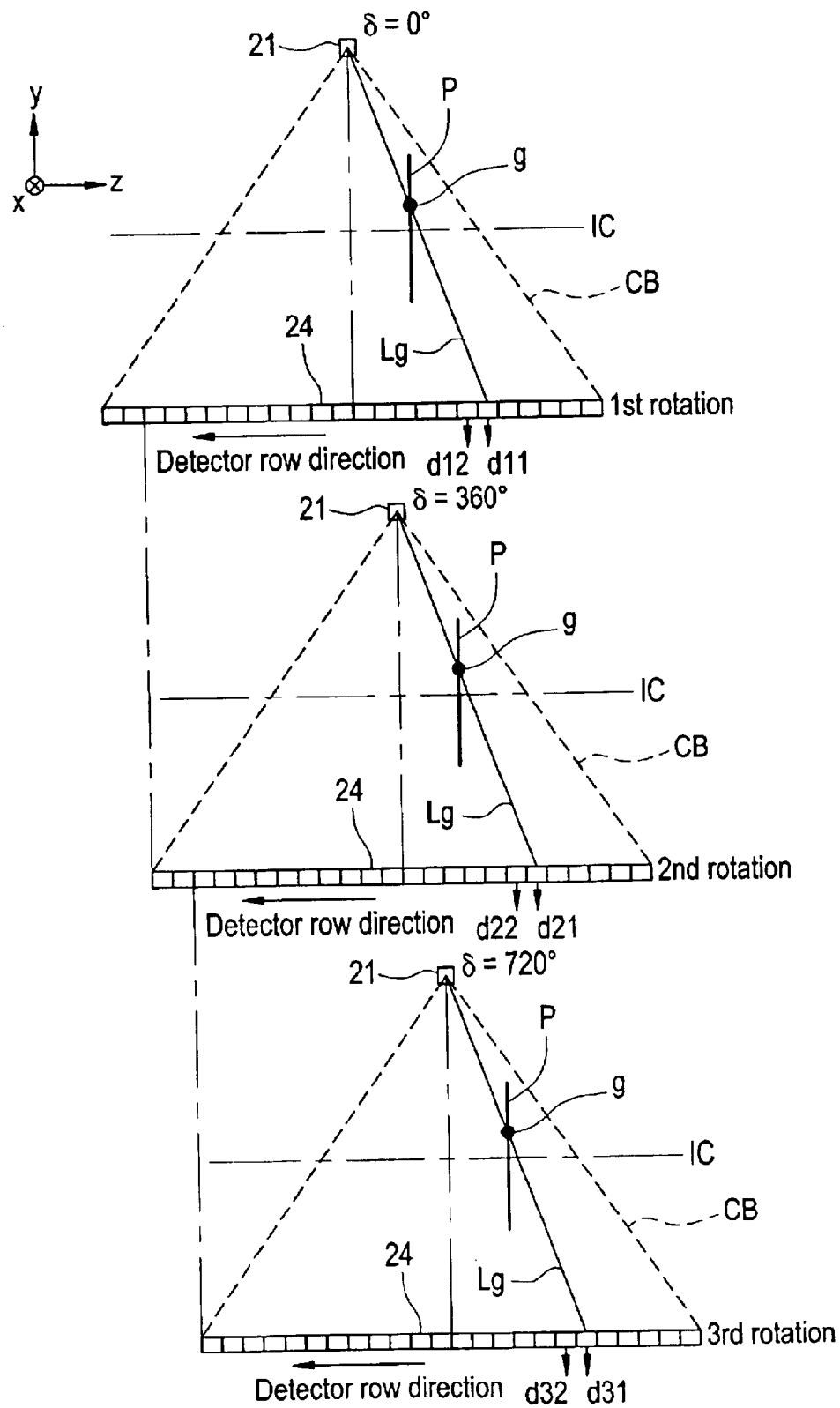
FIG. 8 is a conceptual diagram showing raw data corresponding to a reconstruction field in the second embodiment.

At Step B2, raw data d11 and d12 corresponding to a pixel g in a reconstruction field P are obtained for a first rotation as shown in FIG. 8. Specifically, the raw data d11 and d12 are obtained from two detector rows that lie closest to a point at which a straight line Lg passing through a focal spot of the X-ray tube 21 and the pixel g in the reconstruction field P intersects the multi-row detector 24. The raw data d11 and d12 are then multiplied by cone-beam reconstruction weights Wa and Wb and Z-filter weights wa and wb and are added to calculate a projection datum Dg1 corresponding to the pixel g in the reconstruction field P.

The cone-beam reconstruction weight Wa is defined as $(r1/r0)^2$, where the distance from the focal spot of the X-ray tube 21 to a detector row j, channel i of the multi-row detector 24 that corresponds to the raw data d11 is represented as r0, and the distance from the focal spot of the X-ray tube 21 to the pixel g in the reconstruction field corresponding to the raw data d1 is represented as r1.

The cone-beam reconstruction weight Wb is similarly defined.

Figure 16:
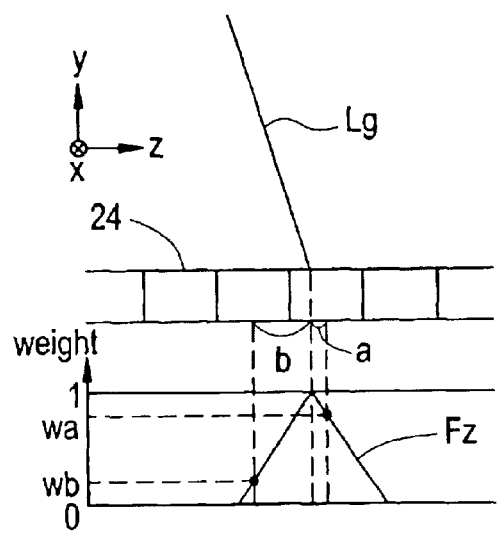
FIG. 16 is a conceptual diagram showing a conventional Z-filter.

The Z-filter weights wa and wb are defined as wa=b/(a+b) and wb=a/(a+b), where the distance between the point at which the straight line Lg intersects the multi-row detector 24 and a point corresponding to the raw data d11 as measured in the Z-direction of the detector is represented as a, and the distance between the point at which the straight line Lg intersects the multi-row detector 24 and a point corresponding to the raw data d12 as measured in the Z-direction of the detector is represented as b. These are weights as delineated by the Z-filter Fz shown in FIG. 16.

Referring again to FIG. 7, at Step B3, raw data d21 and d22 corresponding to the pixel g in the reconstruction field P are obtained for a second rotation as shown in FIG. 8. Specifically, the raw data d21 and d22 are obtained from two detector rows that lie closest to a point at which the straight line Lg passing through the focal spot of the X-ray tube 21 and the pixel g in the reconstruction field P intersects the multi-row detector 24. The raw data d21 and d22 are then multiplied by cone-beam reconstruction weights Wa and Wb and Z-filter weights wa and wb and are added to calculate a projection datum Dg2 corresponding to the pixel g in the reconstruction field P.

The cone-beam reconstruction weight Wa is defined as $(r1/r0)^2$, where the distance from the focal spot of the X-ray tube 21 to a detector row j, channel i of the multi-row detector 24 that corresponds to the raw data d21 is represented as r0, and the distance from the focal spot of the X-ray tube 21 to the pixel g in the reconstruction field corresponding to the raw data d21 is represented as r1.

The cone-beam reconstruction weight Wb is similarly defined.

The Z-filter weights wa and wb are defined as wa=b/(a+b) and wb=a/(a+b), where the distance between the point at which the straight line Lg intersects the multi-row detector 24 and a point corresponding to the raw data d21 as measured in the Z-direction of the detector is represented as a, and the distance between the point at which the straight line Lg intersects the multi-row detector 24 and a point corresponding to the raw data d22 as measured in the Z-direction of the detector is represented as b. These are weights as delineated by the Z-filter Fz shown in FIG. 16.

Referring again to FIG. 7, at Step B4, raw data d31 and d32 corresponding to the pixel g in the reconstruction field P are obtained for a third rotation as shown in FIG. 8. Specifically, the raw data d31 and d32 are obtained from two detector rows that lie closest to a point at which the straight line Lg passing through the focal spot of the X-ray tube 21 and the pixel g in the reconstruction field P intersects the multi-row detector 24. The raw data d31 and d32 are then multiplied by cone-beam reconstruction weights Wa and Wb and Z-filter weights wa and wb and are added to calculate a projection datum Dg3 corresponding to the pixel g in the reconstruction field P.

The cone-beam reconstruction weight Wa is defined as $(r1/r0)^2$, where the distance from the focal spot of the X-ray tube 21 to a detector row j, channel i of the multi-row detector 24 that corresponds to the raw data d31 is represented as r0, and the distance from the focal spot of the X-ray tube 21 to the pixel g in the reconstruction field corresponding to the raw data d31 is represented as r1.

The cone-beam reconstruction weight Wb is similarly defined.

The Z-filter weights wa and wb are defined as wa=b/(a+b) and wb=a/(a+b), where the distance between the point at which the straight line Lg intersects the multi-row detector 24 and a point corresponding to the raw data d31 as measured in the Z-direction of the detector is represented as a, and the distance between the point at which the straight line Lg intersects the multi-row detector 24 and a point corresponding to the raw data d32 as measured in the Z-direction of the detector is represented as b. These are weights as delineated by the Z-filter Fz shown in FIG. 16.

Referring again to FIG. 7, at Step B5, the projection data Dg1–Dg3 are multiplied by the Z-filter weights w1–w3 and are added to calculate a projection datum Dg corresponding to the pixel g in the reconstruction field P.

The Z-filter weights w1–w3 are defined by a Z-filter for three-point interpolation known in the art. When the Z-filter is of the simple addition type, w1=w2=w3.

At Step B6, backprojection processing is applied to the projection datum Dg to calculate a pixel datum Gg.

According to the multi-row detector X-ray CT apparatus of the second embodiment, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained. Furthermore, since a projection datum for each rotation is generated using a Z-filter for two-point interpolation, calculation is simplified.

Although raw data for three rotations are employed in this embodiment, the process can be similarly applied to a case in which raw data for two or four or more consecutive rotations are employed.

Third Embodiment

Figure 9:
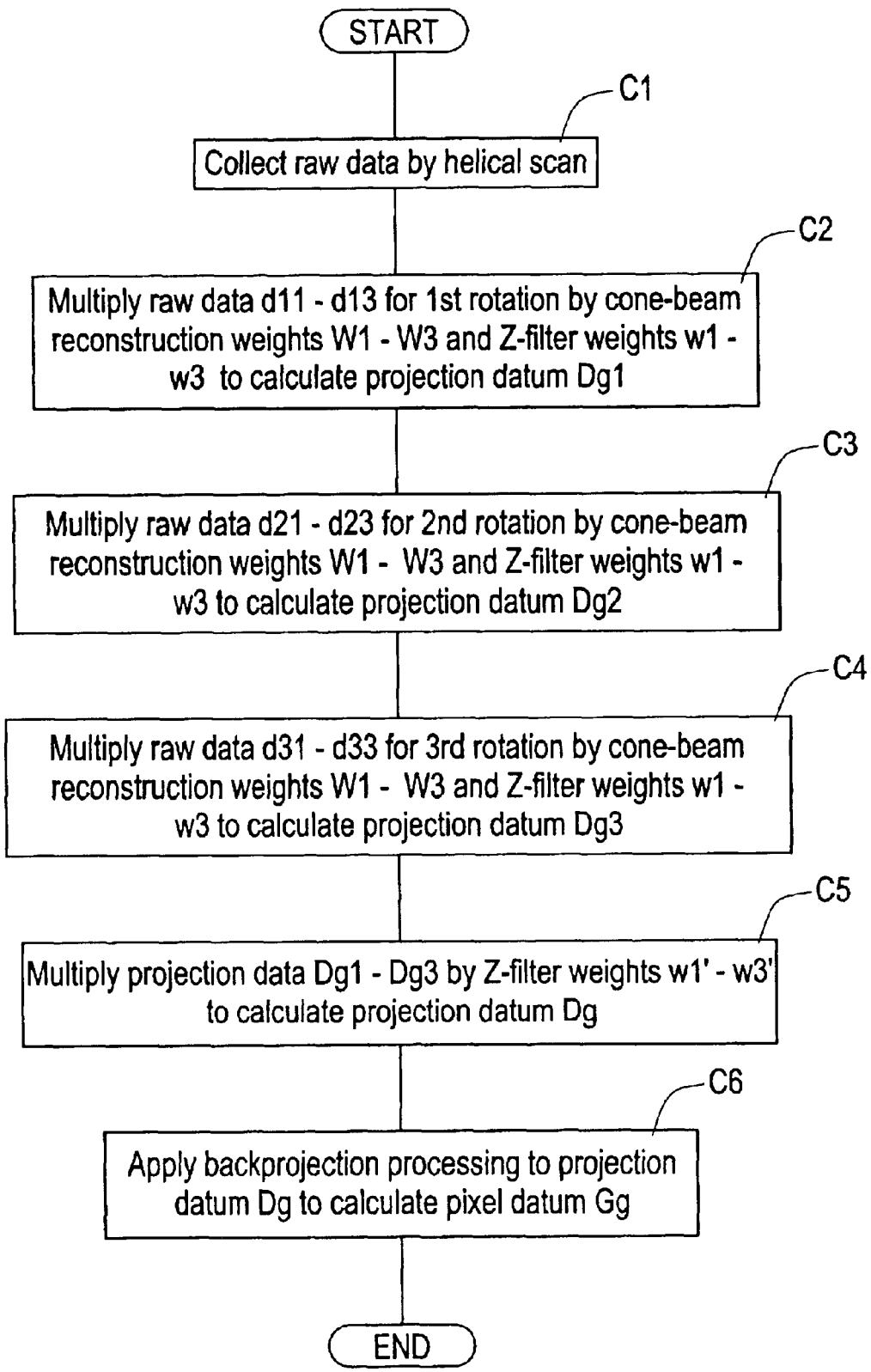
FIG. 9 is a flow chart showing pixel data generating processing in accordance with a third embodiment.

FIG. 9 is a flow chart showing image data generating processing in accordance with a third embodiment.

At Step C1, raw data dj(view, δ, i) represented by a view angle view, relative angular difference δ, detector row index j, and channel index i are collected while rotating the X-ray tube 21 and multi-row detector 24 around the subject to be imaged and linearly moving the cradle 12.

The relative angular difference δ is a parameter indicating the number of rotations at the same view angle, and for example, is represented as δ=0° for a first rotation, δ=360° for a second rotation, δ=720° for a third rotation, and so forth.

The cradle 12 is configured to linearly move by an amount corresponding to three detector rows per rotation.

Figure 10:
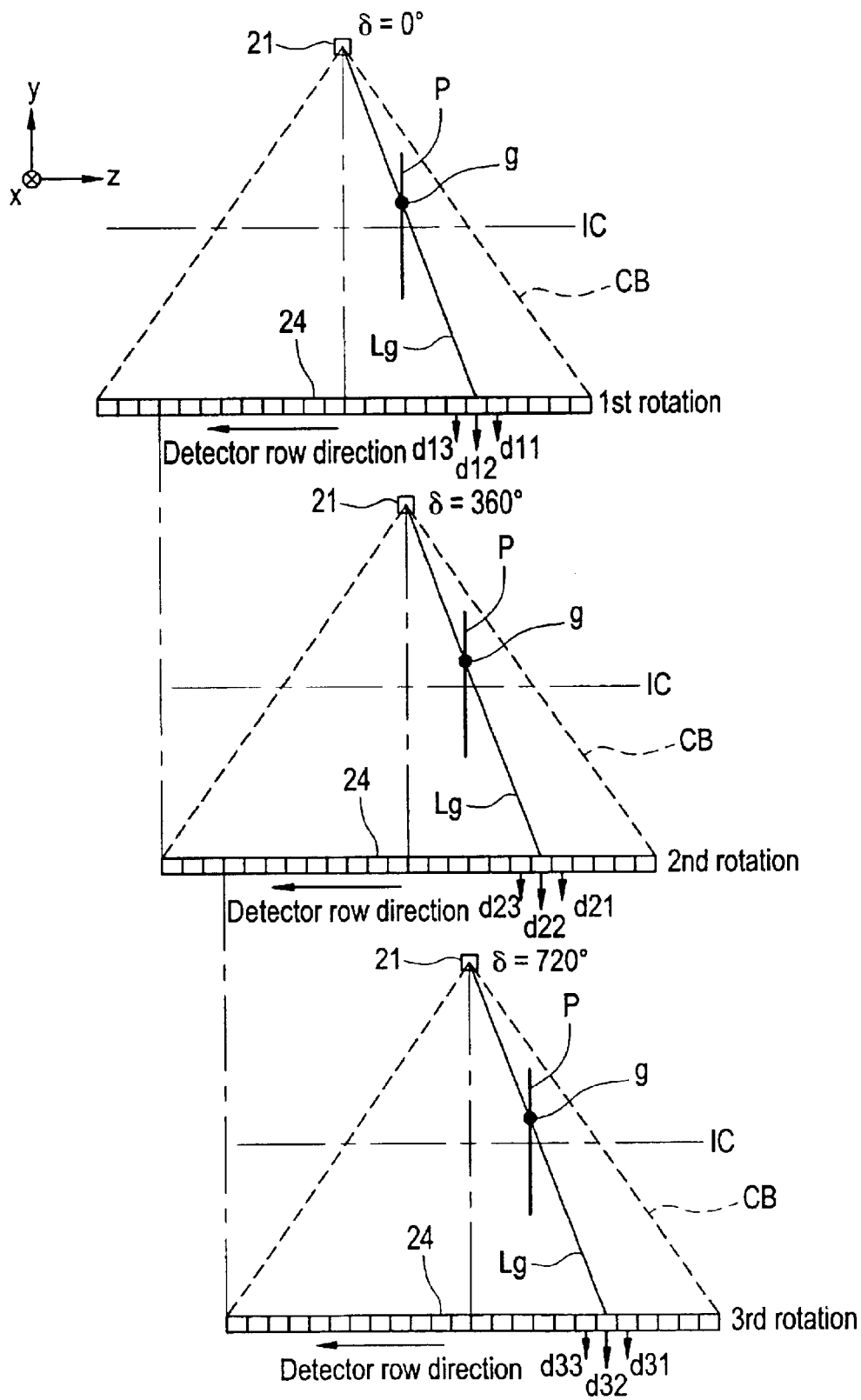
FIG. 10 is a conceptual diagram showing raw data corresponding to a reconstruction field in the third embodiment.

At Step C2, raw data d11–d13 corresponding to a pixel g in a reconstruction field P are obtained for a first rotation as shown in FIG. 10. Specifically, the raw data d11–d13 are obtained from three detector rows that lie closest to a point at which a straight line Lg passing through a focal spot of the X-ray tube 21 and the pixel g in the reconstruction field P intersects the multi-row detector 24. The raw data d11–d13 are then multiplied by cone-beam reconstruction weights W1–W3 and Z-filter weights w1–w3 and are added to calculate a projection datum Dg1 corresponding to the pixel g in the reconstruction field P.

The cone-beam reconstruction weight W1 is defined as $(r1/r0)^2$, where the distance from the focal spot of the X-ray tube 21 to a detector row j, channel i of the multi-row detector 24 that corresponds to the raw data d11 is represented as r0, and the distance from the focal spot of the X-ray tube 21 to the pixel g in the reconstruction field corresponding to the raw data d11 is represented as r1.

The cone-beam reconstruction weights W2 and W3 are similarly defined.

The Z-filter weights w1–w3 are defined by a Z-filter for three-point interpolation known in the art.

Referring again to FIG. 9, at Step C3, raw data d21–d23 corresponding to the pixel g in the reconstruction field P are obtained for a second rotation as shown in FIG. 10. Specifically, the raw data d21–d23 are obtained from three detector rows that lie closest to a point at which the straight line Lg passing through the focal spot of the X-ray tube 21 and the pixel g in the reconstruction field P intersects the multi-row detector 24. The raw data d21–d23 are then multiplied by cone-beam reconstruction weights W1–W3 and Z-filter weights w1–w3 and are added to calculate a projection datum Dg2 corresponding to the pixel g in the reconstruction field P.

The cone-beam reconstruction weight W1 is defined as $(r1/r0)^2$, where the distance from the focal spot of the X-ray tube 21 to a detector row j, channel i of the multi-row detector 24 that corresponds to the raw data d21 is represented as r0, and the distance from the focal spot of the X-ray tube 21 to the pixel g in the reconstruction field corresponding to the raw data d21 is represented as r1.

The cone-beam reconstruction weights W2 and W3 are similarly defined.

The Z-filter weights w1–w3 are defined by a Z-filter for three-point interpolation known in the art.

Referring again to FIG. 9, at Step C4, raw data d31–d33 corresponding to the pixel g in the reconstruction field P are obtained for a third rotation as shown in FIG. 10. Specifically, the raw data d31–d33 are obtained from three detector rows that lie closest to a point at which the straight line Lg passing through the focal spot of the X-ray tube 21 and the pixel g in the reconstruction field P intersects the multi-row detector 24. The raw data d31–d33 are then multiplied by cone-beam reconstruction weights W1–W3 and Z-filter weights w1–w3 and are added to calculate a projection datum Dg3 corresponding to the pixel g in the reconstruction field P.

The cone-beam reconstruction weight W1 is defined as $(r1/r0)^2$, where the distance from the focal spot of the X-ray tube 21 to a detector row j, channel i of the multi-row detector 24 that corresponds to the raw data d31 is represented as r0, and the distance from the focal spot of the X-ray tube 21 to the pixel g in the reconstruction field corresponding to the raw data d31 is represented as r1.

The cone-beam reconstruction weights W2 and W3 are similarly defined.

The Z-filter weights w1–w3 are defined by a Z-filter for three-point interpolation known in the art.

Referring again to FIG. 9, at Step C5, the projection data Dg1–Dg3 are multiplied by Z-filter weights w1'–w3' and are added to calculate a projection datum Dg corresponding to the pixel g in the reconstruction field P.

The Z-filter weights w1'–w3' are defined by a Z-filter for three-point interpolation known in the art. When the Z-filter is of the simple addition type, w1'=w2'=w3'.

At Step C6, backprojection processing is applied to the projection datum Dg to calculate a pixel datum Gg.

According to the multi-row detector X-ray CT apparatus of the third embodiment, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained. Furthermore, the slice thickness corresponding to projection data for each rotation can be made larger than the size of the detector as measured in the Z-axis direction.

Although the raw data of three adjacent detector rows are employed in this embodiment, the process can be similarly applied to a case in which raw data of four or more adjacent detector rows are employed. Moreover, although raw data for three rotations are employed in this embodiment, the process can be similarly applied to a case in which raw data for two or four or more consecutive rotations are employed.

Fourth Embodiment

Figure 11:
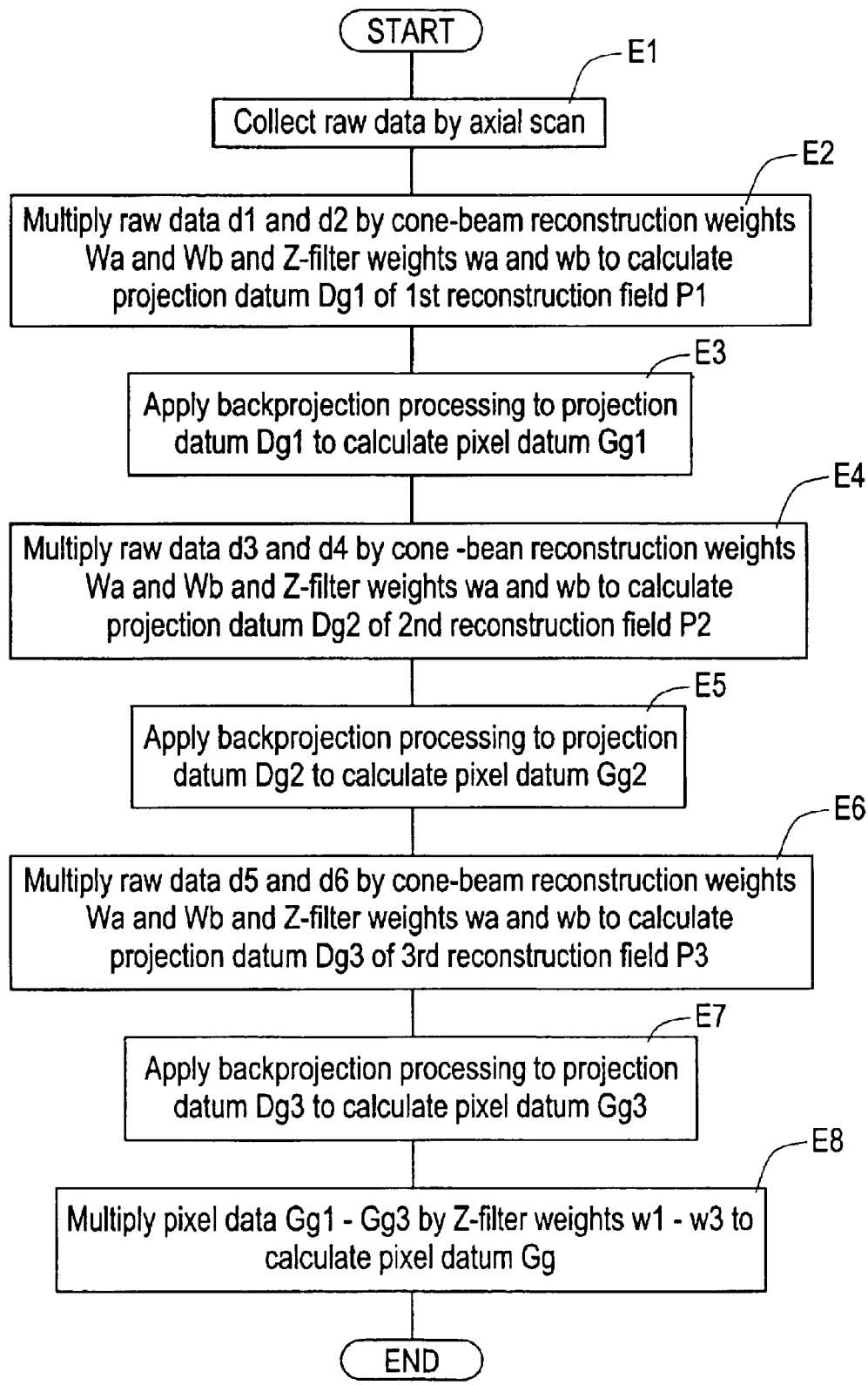
FIG. 11 is a flow chart showing pixel data generating processing in accordance with a fourth embodiment.

FIG. 11 is a flow chart showing image data generating processing in accordance with a fourth embodiment.

At Step E1, raw data dj(view, i) represented by a view angle view, detector row index j, and channel index i are collected while rotating the X-ray tube 21 and multi-row detector 24 around the subject to be imaged.

Figure 12:
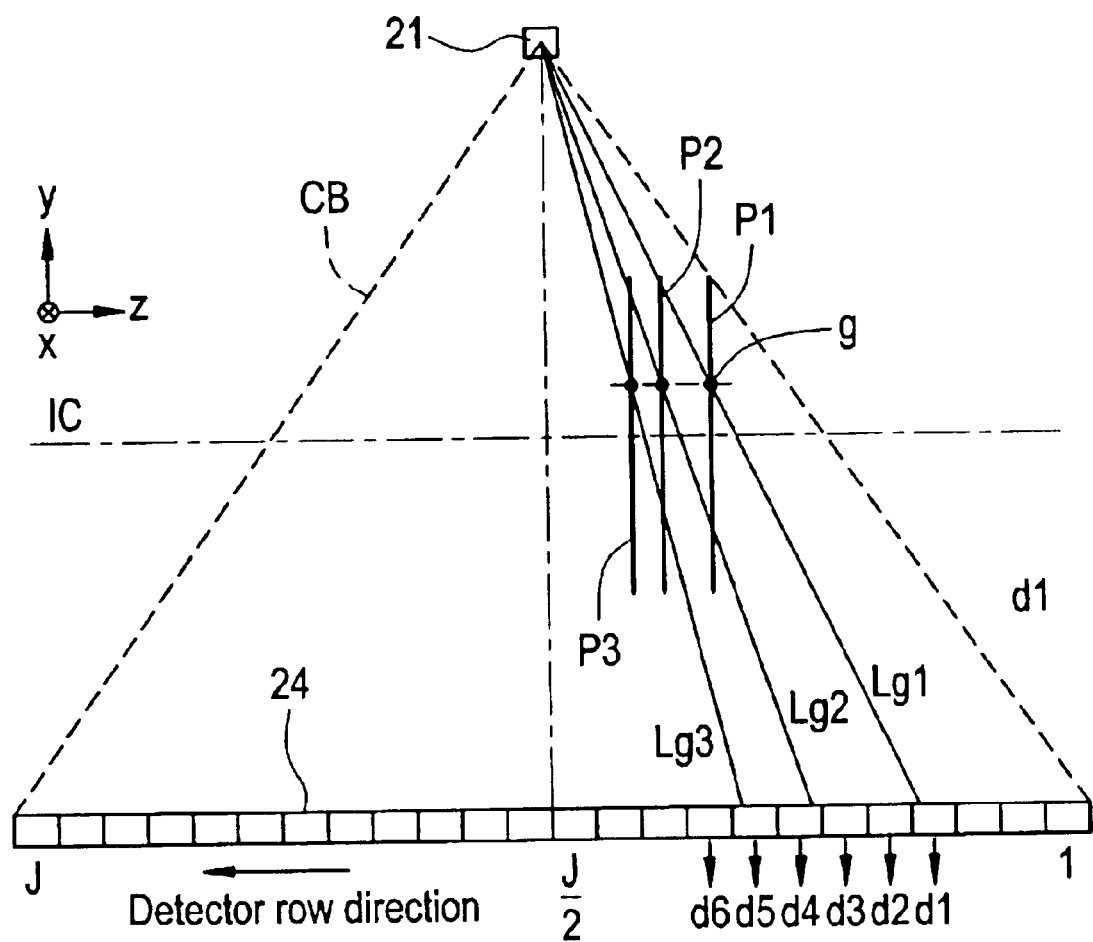
FIG. 12 is a conceptual diagram showing raw data corresponding to reconstruction fields in the fourth embodiment.

At Step E2, raw data d1 and d2 corresponding to a pixel g in a first reconstruction field P1 are obtained as shown in FIG. 12. Specifically, the raw data d1 and d2 are obtained from two detector rows that lie closest to a point at which a straight line Lg1 passing through a focal spot of the X-ray tube 21 and the pixel g in the first reconstruction field P1 intersects the multi-row detector 24. The raw data d1 and d2 are then multiplied by cone-beam reconstruction weights Wa and Wb and Z-filter weights wa and wb and are added to calculate a projection datum Dg1 corresponding to the pixel g in the first reconstruction field P1.

The cone-beam reconstruction weight Wa is defined as $(r1/r0)^2$, where the distance from the focal spot of the X-ray tube 21 to a detector row j, channel i of the multi-row detector 24 that corresponds to the raw data d1 is represented as r0, and the distance from the focal spot of the X-ray tube 21 to the pixel g in the reconstruction field corresponding to the raw data d1 is represented as r1.

The cone-beam reconstruction weight Wb is similarly defined.

The Z-filter weights wa and wb are defined as wa=b/(a+b) and wb=a/(a+b), where the distance between the point at which the straight line Lg1 intersects the multi-row detector 24 and a point corresponding to the raw data d1 as measured in the Z-direction of the detector is represented as a, and the distance between the point at which the straight line Lg1 intersects the multi-row detector 24 and a point corresponding to the raw data d2 as measured in the Z-direction of the detector is represented as b. These are weights as delineated by the Z-filter Fz shown in FIG. 16.

Referring again to FIG. 11, at Step E3, backprojection processing is applied to the projection datum Dg1 to calculate a pixel datum Gg1.

At Step E4, raw data d3 and d4 corresponding to a pixel g in a second reconstruction field P2 are obtained as shown in FIG. 12. Specifically, the raw data d3 and d4 are obtained from two detector rows that lie closest to a point at which a straight line Lg2 passing through the focal spot of the X-ray tube 21 and the pixel g in the second reconstruction field P2 intersects the multi-row detector 24. The raw data d3 and d4 are then multiplied by cone-beam reconstruction weights Wa and Wb and Z-filter weights wa and wb and are added to calculate a projection datum Dg2 corresponding to the pixel g in the second reconstruction field P2.

The cone-beam reconstruction weight Wa is defined as $(r1/r0)^2$, where the distance from the focal spot of the X-ray tube 21 to a detector row j, channel i of the multi-row detector 24 that corresponds to the raw data d3 is represented as r0, and the distance from the focal spot of the X-ray tube 21 to the pixel g in the reconstruction field corresponding to the raw data d3 is represented as r1.

The cone-beam reconstruction weight Wb is similarly defined.

The Z-filter weights wa and wb are defined as wa=b/(a+b) and wb=a/(a+b), where the distance between the point at which the straight line Lg2 intersects the multi-row detector 24 and a point corresponding to the raw data d3 as measured in the Z-direction of the detector is represented as a, and the distance between the point at which the straight line Lg2 intersects the multi-row detector 24 and a point corresponding to the raw data d4 as measured in the Z-direction of the detector is represented as b. These are weights as delineated by the Z-filter Fz shown in FIG. 16.

Referring again to FIG. 11, at Step E5, backprojection processing is applied to the projection datum Dg2 to calculate a pixel datum Gg2.

At Step E6, raw data d5 and d6 corresponding to a pixel g in a third reconstruction field P3 are obtained as shown in FIG. 12. Specifically, the raw data d5 and d6 are obtained from two detector rows that lie closest to a point at which a straight line Lg3 passing through the focal spot of the X-ray tube 21 and the pixel g in the third reconstruction field P3 intersects the multi-row detector 24. The raw data d5 and d6 are then multiplied by cone-beam reconstruction weights Wa and Wb and Z-filter weights wa and wb and are added to calculate a projection datum Dg3 corresponding to the pixel g in the third reconstruction field P3.

The cone-beam reconstruction weight Wa is defined as $(r1/r0)^2$, where the distance from the focal spot of the X-ray tube 21 to a detector row j, channel i of the multi-row detector 24 that corresponds to the raw data d5 is represented as r0, and the distance from the focal spot of the X-ray tube 21 to the pixel g in the reconstruction field corresponding to the raw data d5 is represented as r1.

The cone-beam reconstruction weight Wb is similarly defined.

The Z-filter weights wa and wb are defined as wa=b/(a+b) and wb=a/(a+b), where the distance between the point at which the straight line Lg3 intersects the multi-row detector 24 and a point corresponding to the raw data d5 as measured in the Z-direction of the detector is represented as a, and the distance between the point at which the straight line Lg3 intersects the multi-row detector 24 and a point corresponding to the raw data d6 as measured in the Z-direction of the detector is represented as b. These are weights as delineated by the Z-filter Fz shown in FIG. 16.

Referring again to FIG. 11, at Step E7, backprojection processing is applied to the projection datum Dg3 to calculate a pixel datum Gg3.

At Step E8, the pixel data Gg1–Gg3 are multiplied by Z-filter weights w1–w3 and are added to generate a pixel datum Gg.

The Z-filter weights w1–w3 are defined by a Z-filter for three-point interpolation known in the art. When the Z-filter is of the simple addition type, w1=w2=w3.

According to the multi-row detector X-ray CT apparatus of the fourth embodiment, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained. Furthermore, images having a small slice thickness can be simultaneously obtained.

Although the three reconstruction fields P1–P3 are employed in this embodiment, the process can be similarly applied to a case in which two or four or more proximate reconstruction fields are employed.

Moreover, although the projection datum for each reconstruction field is obtained from raw data of two adjacent detector rows, raw data of three or more adjacent detector rows may be employed.

Furthermore, although the axial scan is conducted, a helical scan may be conducted.

Fifth Embodiment

Figure 13:
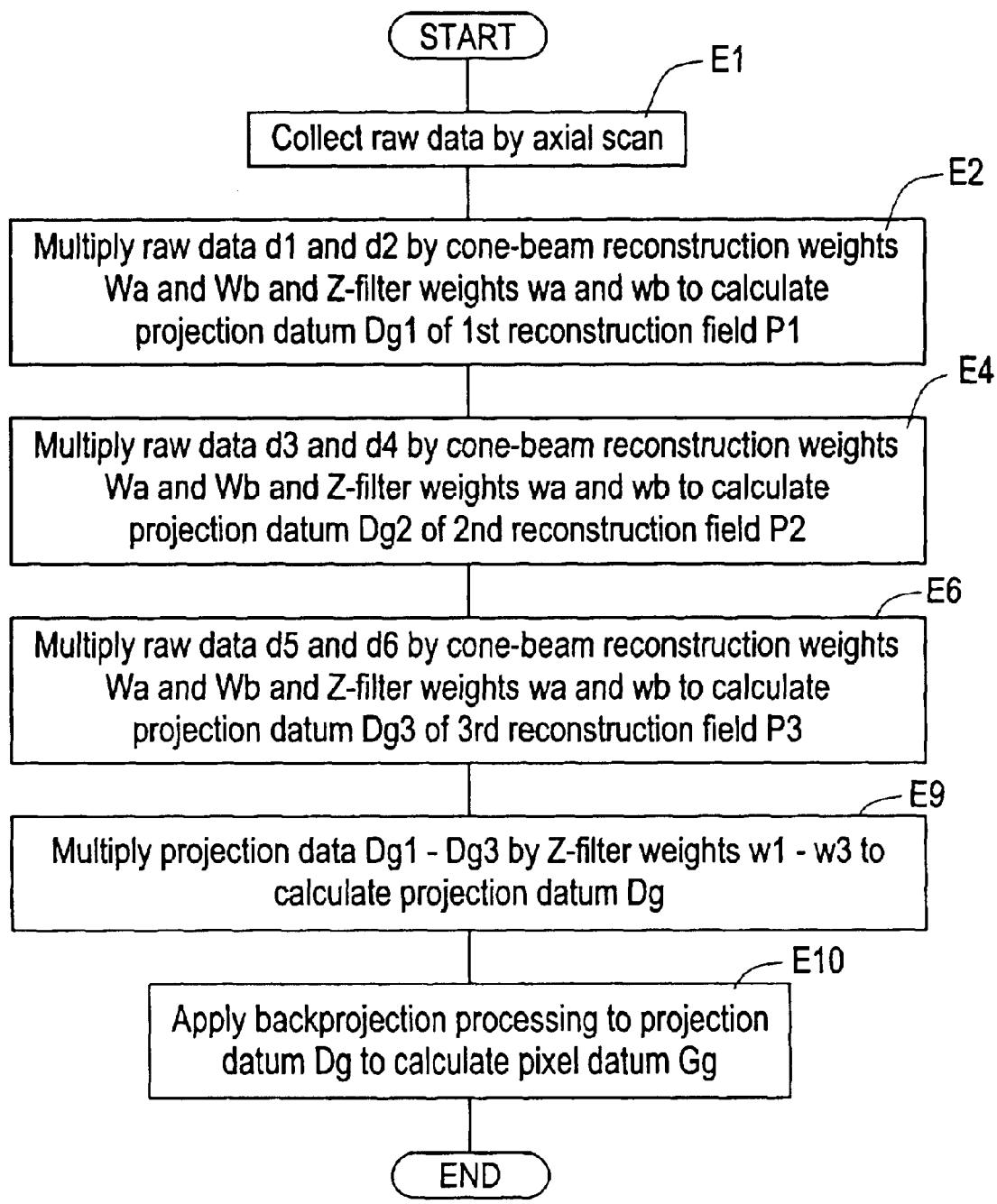
FIG. 13 is a flow chart showing pixel data generating processing in accordance with a fifth embodiment.
Figure 14:
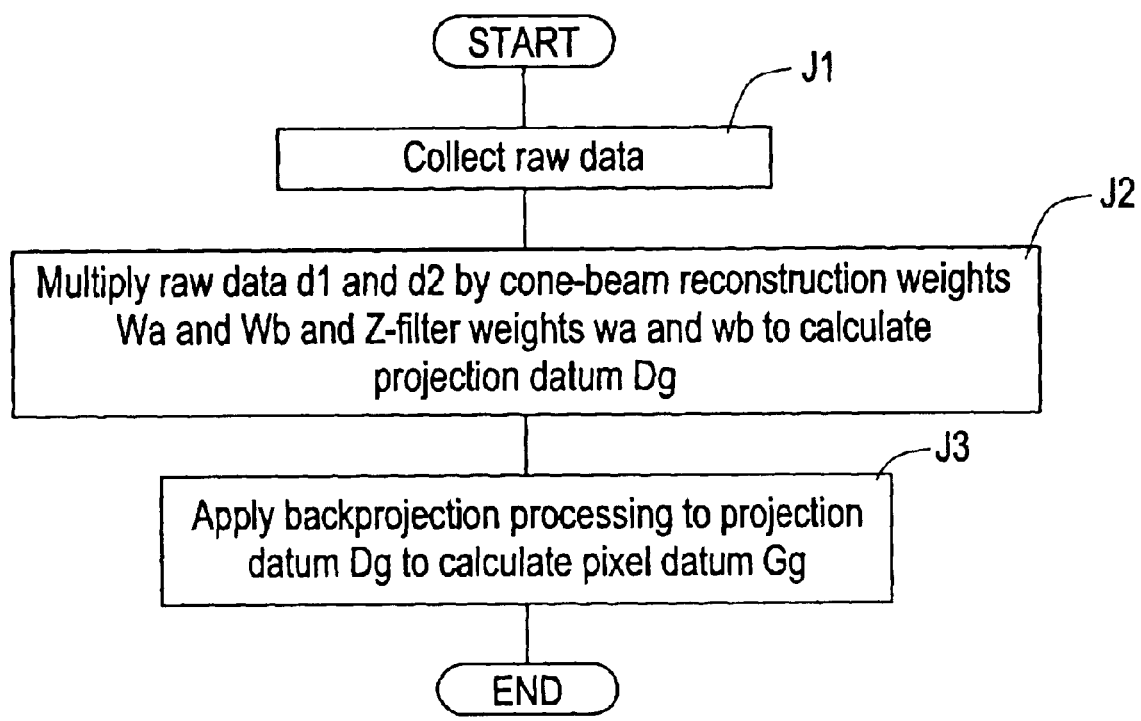
FIG. 14 is a flow chart showing conventional pixel data generating processing.
Figure 15:
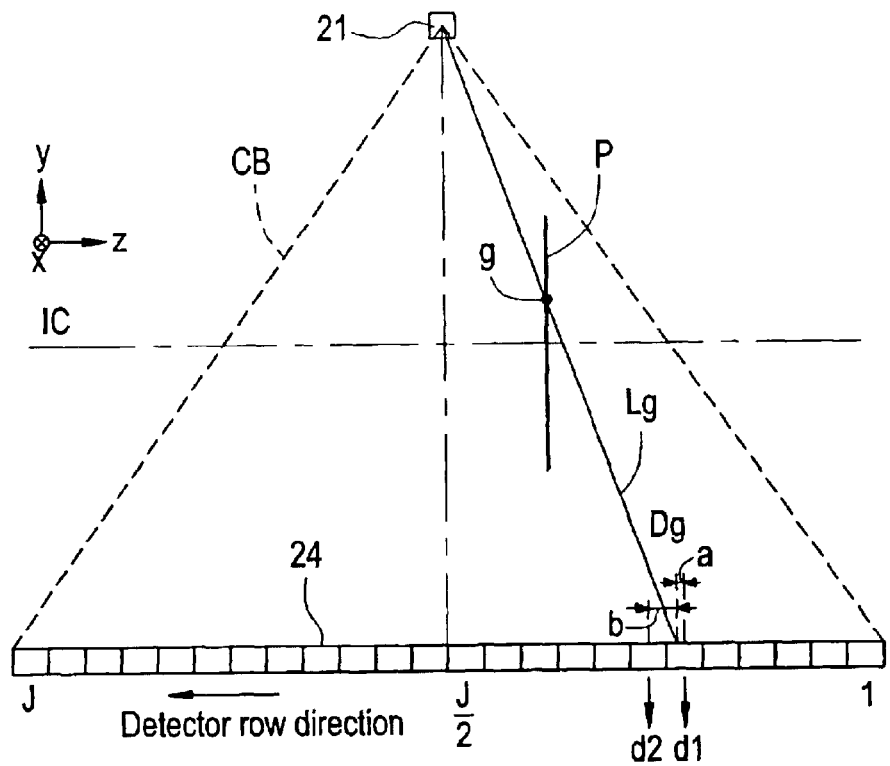
FIG. 15 is a conceptual diagram showing raw data corresponding to a conventional reconstruction field.

FIG. 13 is a flow chart showing image data generating processing in accordance with a fifth embodiment.

At Step E1, raw data dj(view, i) represented by a view angle view, detector row index j, and channel index i are collected while rotating the X-ray tube 21 and multi-row detector 24 around the subject to be imaged.

At Step E2, raw data d1 and d2 corresponding to a pixel g in a first reconstruction field P1 are obtained as shown in FIG. 12. Specifically, the raw data d1 and d2 are obtained from two detector rows that lie closest to a point at which a straight line Lg1 passing through a focal spot of the X-ray tube 21 and the pixel g in the first reconstruction field P1 intersects the multi-row detector 24. The raw data d1 and d2 are then multiplied by cone-beam reconstruction weights Wa and Wb and Z-filter weights wa and wb and are added to calculate a projection datum Dg1 corresponding to the pixel g in the first reconstruction field P1.

The cone-beam reconstruction weight Wa is defined as $(r1/r0)^2$, where the distance from the focal spot of the X-ray tube 21 to a detector row j, channel i of the multi-row detector 24 that corresponds to the raw data d1 is represented as r0, and the distance from the focal spot of the X-ray tube 21 to the pixel g in the reconstruction field corresponding to the raw data d1 is represented as r1.

The cone-beam reconstruction weight wb is similarly defined.

The Z-filter weights wa and wb are defined as wa=b/(a+b) and wb=a/(a+b), where the distance between the point at which the straight line Lg1 intersects the multi-row detector 24 and a point corresponding to the raw data d1 as measured in the Z-direction of the detector is represented as a, and the distance between the point at which the straight line Lg1 intersects the multi-row detector 24 and a point corresponding to the raw data d2 as measured in the Z-direction of the detector is represented as b. These are weights as delineated by the Z-filter Fz shown in FIG. 16.

Referring again to FIG. 13, at Step E4, raw data d3 and d4 corresponding to a pixel g in a second reconstruction field P2 are obtained as shown in FIG. 12. Specifically, the raw data d3 and d4 are obtained from two detector rows that lie closest to a point at which a straight line Lg2 passing through the focal spot of the X-ray tube 21 and the pixel g in the second reconstruction field P2 intersects the multi-row detector 24. The raw data d3 and d4 are then multiplied by cone-beam reconstruction weights Wa and Wb and Z-filter weights wa and wb and are added to calculate a projection datum Dg2 corresponding to the pixel g in the second reconstruction field P2.

The cone-beam reconstruction weight Wa is defined as $(r1/r0)^2$, where the distance from the focal spot of the X-ray tube 21 to a detector row j, channel i of the multi-row detector 24 that corresponds to the raw data d3 is represented as r0, and the distance from the focal spot of the X-ray tube 21 to the pixel g in the reconstruction field corresponding to the raw data d3 is represented as r1.

The cone-beam reconstruction weight Wb is similarly defined.

The Z-filter weights wa and wb are defined as wa=b/(a+b) and wb=a/(a+b), where the distance between the point at which the straight line Lg2 intersects the multi-row detector 24 and a point corresponding to the raw data d3 as measured in the Z-direction of the detector is represented as a, and the distance between the point at which the straight line Lg2 intersects the multi-row detector 24 and a point corresponding to the raw data d4 as measured in the Z-direction of the detector is represented as b. These are weights as delineated by the Z-filter Fz shown in FIG. 16.

Referring again to FIG. 13, at Step E6, raw data d5 and d6 corresponding to a pixel g in a third reconstruction field P3 are obtained as shown in FIG. 12. Specifically, the raw data d5 and d6 are obtained from two detector rows that lie closest to a point at which a straight line Lg3 passing through the focal spot of the X-ray tube 21 and the pixel g in the third reconstruction field P3 intersects the multi-row detector 24. The raw data d5 and d6 are then multiplied by cone-beam reconstruction weights Wa and Wb and Z-filter weights wa and wb and are added to calculate a projection datum Dg3 corresponding to the pixel g in the third reconstruction field P3.

The cone-beam reconstruction weight Wa is defined as $(r1/r0)^2$, where the distance from the focal spot of the X-ray tube 21 to a detector row j, channel i of the multi-row detector 24 that corresponds to the raw data d5 is represented as r0, and the distance from the focal spot of the X-ray tube 21 to the pixel g in the reconstruction field corresponding to the raw data d5 is represented as r1.

The cone-beam reconstruction weight Wb is similarly defined.

The Z-filter weights wa and wb are defined as wa=b/(a+b) and wb=a/(a+b), where the distance between the point at which the straight line Lg3 intersects the multi-row detector 24 and a point corresponding to the raw data d5 as measured in the Z-direction of the detector is represented as a, and the distance between the point at which the straight line Lg3 intersects the multi-row detector 24 and a point corresponding to the raw data d6 as measured in the Z-direction of the detector is represented as b. These are weights as delineated by the Z-filter Fz shown in FIG. 16.

Referring again to FIG. 13, at Step E9, the projection data Dg1–Dg3 are multiplied by Z-filter weights w1–w3 and are added to calculate a projection datum Dg.

The Z-filter weights w1–w3 are defined by a Z-filter for three-point interpolation known in the art. When the Z-filter is of the simple addition type, w1=w2=w3.

At Step E10, backprojection processing is applied to the projection datum Dg to calculate a pixel datum Dg.

According to the multi-row detector X-ray CT apparatus of the fifth embodiment, an image having a large slice thickness, such as a thickness twice or three times the size of the detector as measured in the Z-axis direction, can be obtained. Moreover, an image having an arbitrary slice thickness, such as a thickness 1.2 or 2.5 times the size of the detector as measured in the Z-axis direction, can be obtained. Moreover, processing is simplified as compared with the fourth embodiment, although images having a small slice thickness cannot be simultaneously obtained.

Although the three reconstruction fields P1–P3 are employed in this embodiment, the process can be similarly applied to a case in which two or four or more proximate reconstruction fields are employed.

Moreover, although the projection datum for each reconstruction field is obtained from raw data of two adjacent detector rows, raw data of three or more adjacent detector rows may be employed.

Furthermore, although the axial scan is conducted, a helical scan may be conducted.

Other Embodiments

The aforementioned embodiments may be appropriately combined.

Many widely different embodiments of the invention may be configured without departing from the spirit and the scope of the present invention. It should be understood that the present invention is not limited to the specific embodiments described in the specification, except as defined in the appended claims.

What is claimed is:

1. A multi-row detector X-ray CT apparatus comprising:
   an X-ray tube;
   a multi-row detector having three or more detector rows;
   a scanning device for collecting raw data while rotating at least one of said X-ray tube and said multi-row detector around a subject to be imaged or while rotating at least one of them and at the same time linearly moving both of them relative to the subject to be imaged;
   a projection data generating device for multiplying raw data of three or more adjacent detector rows by cone-beam reconstruction weights and Z-filter weights, and adding the multiplied raw data to obtain one projection datum; and
   a backprojection processing device for applying backprojection processing to the projection data to obtain pixel data.

2. A multi-row detector X-ray CT apparatus comprising:
   an X-ray tube;
   a multi-row detector having two or more detector rows;
   a scanning device for collecting raw data while rotating at least one of said X-ray tube and said multi-row detector around a subject to be imaged or while rotating at least one of them and at the same time linearly moving both of them relative to the subject to be imaged;
   a projection data generating device for generating an i-th projection datum corresponding to a pixel in a reconstruction field from raw data of k adjacent detector rows for an i-th rotation among raw data collected by a helical scan in which k ($\geq 2$) or more rows go forward per rotation, repeating the generation of the i-th projection datum for i=1–n, n$\geq$2, and next multiplying first–n-th projection data by Z-filter weights and adding the multiplied projection data to obtain one projection datum; and
   a backprojection processing device for applying backprojection processing to the projection data to obtain pixel data.

3. The multi-row detector X-ray CT apparatus of claim 2, wherein k=2, and said projection data generating device generates the i-th projection datum by multiplying raw data of two adjacent detector rows by cone-beam reconstruction weights and Z-filter weights, and adding the multiplied raw data.

4. A multi-row detector X-ray CT apparatus comprising:
   an X-ray tube;
   a multi-row detector having two or more detector rows;
   a scanning device for collecting raw data while rotating at least one of said X-ray tube and said multi-row detector around a subject to be imaged or while rotating at least one of them and at the same time linearly moving both of them relative to the subject to be imaged; and
   a pixel data generating device for generating an i-th pixel datum corresponding to a pixel in an i-th reconstruction field from raw data of k (k$\geq$2) adjacent detector rows among the raw data, repeating the generation of the i-th pixel datum for i=1–n, n$\geq$2, and next multiplying first–n-th pixel data by Z-filter weights and adding the multiplied pixel data to obtain one pixel datum.

* * * * *